(12) United States Patent
Zhang et al.

(10) Patent No.: US 9,687,569 B2
(45) Date of Patent: Jun. 27, 2017

(54) THERANOSTIC NANOPARTICLE AND METHODS FOR MAKING AND USING THE NANOPARTICLE

(71) Applicant: University of Washington through its Center for Commercialization, Seattle, WA (US)

(72) Inventors: Miqin Zhang, Bothell, WA (US); Chen Fang, Lynwood, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 654 days.

(21) Appl. No.: 13/969,362

(22) Filed: Aug. 16, 2013

(65) Prior Publication Data

US 2014/0050671 A1 Feb. 20, 2014

Related U.S. Application Data

(60) Provisional application No. 61/684,064, filed on Aug. 16, 2012.

(51) Int. Cl.
| | |
|---|---|
| *A61B 5/055* | (2006.01) |
| *A61K 49/18* | (2006.01) |
| *A61K 9/51* | (2006.01) |
| *A61K 49/00* | (2006.01) |
| *A61K 47/48* | (2006.01) |

(52) U.S. Cl.
CPC ............ *A61K 49/1857* (2013.01); *A61K 9/51* (2013.01); *A61K 47/48861* (2013.01); *A61K 47/48907* (2013.01); *A61K 49/0093* (2013.01)

(58) Field of Classification Search
CPC ...... A61K 9/51; A61K 9/5107; A61K 9/5115; A61K 9/5123; A61K 9/5192
USPC ...................... 424/9.3, 9.32, 9.323, 489, 490
See application file for complete search history.

(56) References Cited

U.S. PATENT DOCUMENTS

| 5,686,113 | A | 11/1997 | Speaker |
| 7,727,969 | B2 | 6/2010 | Farokhzad |
| 8,313,777 | B2 | 11/2012 | Maitra |
| 2004/0220081 | A1 | 11/2004 | Kreitz |
| 2005/0244504 | A1 | 11/2005 | Little |
| 2010/0137975 | A1 | 6/2010 | Wittchow |
| 2012/0258038 | A1 | 10/2012 | Lee |
| 2012/0282172 | A1 | 11/2012 | de Almeida Moreira |
| 2013/0071326 | A1 | 3/2013 | Martinez |

FOREIGN PATENT DOCUMENTS

| WO | 2004/106411 A2 | 12/2004 | |
| WO | WO 2004106411 A2 * | 12/2004 | ............ A61K 9/5138 |
| WO | 2011/112597 A1 | 9/2011 | |
| WO | 2013/012891 A1 | 1/2013 | |

OTHER PUBLICATIONS

Lee et al (Gold, poly(beta-amino ester) nanoparticles for smaller interfering RNA delivery, Nano lett Jun. 2009, 9(6) 2402-2406.*
Meenach et al, Controlled synergistic delivery of paclitaxel and heat from poly(beta-amino ester)/iron oxide-based hydrogel nanocomposites, International Journal of Pharmaceutics 427 (2012) 177-184.*
Lee et al (Gold, Poly ((β-amino ester) Nanoparticles for Small Interfering RNA Delivery; Nano Lett. Jun. 2009; 9 (6) ).*
Meenach et al (Controlled synergistic delivery of paclitaxel and heat from poly(beta-amino ester)/iron oxide-based hydrogel nanocomposites, International Journal of Pharmaceutics 427 (2012) 177-184).*
Abdalla, M.O., et al., "Enhanced Noscapine Delivery Using uPAR—Targeted Optical—MR Imaging Trackable Nanoparticles for Prostate Cancer Therapy," Journal of Controlled Release 149(3):314-322, Feb. 2011. (Author Manuscript provided, PMCID: PMC3179860, available in PMC Feb. 10, 2012, 20 pages).
Anderson, D.G., et al., "Semi-Automated Synthesis and Screening of a Large Library of Degradable Cationic Polymers for Gene Delivery," Angewandte Chemie International Edition 42(27):3153-3158, Jul. 2003.
Chaudhuri, P., et al., "Fullerenol-Cytotoxic Conjugates for Cancer Chemotherapy," ACS Nano 3(9):2505-2514, Sep. 2009.
Fang, C., and M. Zhang, "Nanoparticle-Based Theragnostics: Integrating Diagnostic and Therapeutic Potentials in Nanomedicine," Journal of Controlled Release 146(1):2-5, Aug. 2010. (Author Manuscript provided, PMCID: PMC2914214, available in PMC Aug. 17, 2011,8 pages).
Fang, C., et al., "Functionalization of Iron Oxide Magnetic Nanoparticles With Targeting Ligands: Their Physicochemical Properties and In Vivo Behavior," Nanomedicine 5(9):1357-1369, Nov. 2010. (Author Manuscript provided, PMCID: PMC3057775, available in PMC Nov. 1, 2011, 20 pages).
Fang, C., et al., "Functionalized Nanoparticles With Long-Term Stability in Biological Media," Small 5(14):1637-1641, Jul. 2009.
Gottesman, M.M., et al., "Multidrug Resistance in Cancer: Role of ATP-Dependent Transporters," Nature Reviews: Cancer 2(1):48-58, Jan. 2002.
Guo, M., et al., "Multilayer Nanoparticles With a Magnetite Core and a Polycation Inner Shell as pH-Responsive Carriers for Drug Delivery," Nanoscale 2(3):434-441, Mar. 2010.

(Continued)

*Primary Examiner* — Micah-Paul Young
(74) *Attorney, Agent, or Firm* — Christensen O'Connor Johnson Kindness PLLC; Juan Zheng; George Renzoni

(57) ABSTRACT

Nanoparticle having a poly(beta-amino ester) coating. The poly(beta-amino ester) coating includes one or more therapeutic agents that can be delivered by the particle and one or more anchoring groups that couple the polymer to the nanoparticle's core surface. In certain embodiments, the poly(beta-amino ester) includes one or more polyalkylene oxide groups. The poly(beta-amino ester) can further include a targeting agent to target the nanoparticle to a site of interest and a diagnostic agent that allows for imaging of the particle. Methods for making and using the nanoparticles are also provided.

20 Claims, 8 Drawing Sheets

(8 of 8 Drawing Sheet(s) Filed in Color)

(56) References Cited

OTHER PUBLICATIONS

Guthi, J.S., et al., "MRI-Visible Micellar Nanomedicine for Targeted Drug Delivery to Lung Cancer Cells," Molecular Pharmaceutics 7(1):32-40, Feb. 2010. (Author Manuscript provided, PMCID: PMC2891983, available in PMC Jun. 25, 2010, 15 pages).
Huang, Y.-H., et al., "Nanoparticle-Delivered Suicide Gene Therapy Effectively Reduces Ovarian Tumor Burden in Mice," Cancer Research 69(15):6184-6191, Aug. 2009. (Author Manuscript provided, PMCID: PMC2735403, available in PMC Aug. 1, 2010, 17 pages).
Jain, T.K., "Iron Oxide Nanoparticles for Sustained Delivery of Anticancer Agents," Molecular Pharmaceutics 2(3):194-205, May-Jun. 2005.
Kievit, F.M., and M. Zhang, "Surface Engineering of Iron Oxide Nanoparticles for Targeted Cancer Therapy," Accounts of Chemical Research 44(10):853-862, Oct. 2011.
Kievit, F.M., et al., "Chlorotoxin Labeled Magnetic Nanovectors for Targeted Gene Delivery to Glioma," ACS Nano 4(8):4587-4594, Aug. 2010.
Kievit, F.M., et al., "Doxorubicin Loaded Iron Oxide Nanoparticles Overcome Multidrug Resistance in Cancer In Vitro," Journal of Controlled Release 152(1):76-83, May 2011.
Kievit, F.M., et al., "PEI-PEG-Chitosan Copolymer Coated Iron Oxide Nanoparticles for Safe Gene Delivery: Synthesis, Complexation, and Transfection," Advanced Functional Materials 19(14):2244-2251, Jul. 2009. (Author Manuscript provided, PMCID: PMC2756666, available in PMC Jul. 24, 2010, 22 pages).
Kohler, N., et al., "Methotrexate-Immobilized Poly(ethylene glycol) Magnetic Nanoparticles for MR Imaging and Drug Delivery," Small 2(6):785-792, Jun. 2006.
Kohler, N., et al., "Methotrexate-Modified Superparamagnetic Nanoparticles and Their Intracellular Uptake Into Human Cancer Cells," Langmuir 21(19):8858-8864, Sep. 2005.
Koo, H., et al., "In Vivo Targeted Delivery of Nanoparticles for Theranosis," Accounts of Chemical Research 44(10):1018-1028, Oct. 2011.
Lai, J.-R., et al., "Multifunctional Doxorubicin/Superparamagnetic Iron Oxide-Encapsulated Pluronic F127 Micelles Used for Chemotherapy/Magnetic Resonance Imaging," Journal of Applied Physics 107(9):09B318-1-09B318-3, May 2010.
Lammers, T., et al., "Nanotheranostics and Image-Guided Drug Delivery: Current Concepts and Future Directions," Molecular Pharmaceutics 7(6):1899-1912, Dec. 2010.
Lammers, T., et al., "Theranostic Nanomedicine," Accounts of Chemical Research 44(10):1029-1038, Oct. 2011.
Lee, J.-S., et al., "Gold, Poly(β-amino ester) Nanoparticles for Small Interfering RNA Delivery," Nano Letters 9(6):2402-2406, Jun. 2009.
Lee, Y., et al., "Bioinspired Surface Immobilization of Hyaluronic Acid on Monodisperse Magnetite Nanocrystals for Targeted Cancer Imaging," Advanced Materials 20(21):4154-4157, Nov. 2008.
Liu, H.-L., et al., "Magnetic Resonance Monitoring of Focused Ultrasound/Magnetic Nanoparticle Targeting Delivery of Therapeutic Agents to the Brain," Proceedings of the National Academy of Sciences of the USA (PNAS) 107(34):15205-15210, Aug. 2010.
MacKay, J.A., et al., "Self-Assembling Chimeric Polypeptide—Doxorubicin Conjugate Nanoparticles That Abolish Tumours After a Single Injection," Nature Materials 8(12):993-999, Dec. 2009.
Nitiss, J.L., "Targeting DNA Topoisomerase II in Cancer Chemotherapy," Nature Reviews: Cancer 9(5):338-350, May 2009. (Author Manuscript provided, PMCID: PMC2748742, available in PMC Nov. 1, 2009, 27 pages).
Pack, D.W., et al., "Design and Development of Polymers for Gene Delivery," Nature Reviews: Drug Discovery 4(7):581-593, Jul. 2005.
Peer, D., et al., "Nanocarriers as an Emerging Platform for Cancer Therapy," Nature Nanotechnology 2(12):751-760, Dec. 2007.
Petros, R.A., and J.M. DeSimone, "Strategies in the Design of Nanoparticles for Therapeutic Applications," Nature Reviews: Drug Discovery 9(8):615-627, Aug. 2010.
Sanson, C., et al., "Doxorubicin Loaded Magnetic Polymersomes: Theranostic Nanocarriers for MR Imaging and Magneto-Chemotherapy," ACS Nano 5(2):1122-1140, Feb. 2011.
Shen, Y., et al., "Degradable Poly(β-amino ester) Nanoparticles for Cancer Cytoplasmic Drug Delivery," Nanomedicine 5(2):192-201, Jun. 2009.
Subayev, V.I., et al., "Magnetic Nanoparticles for Theragnostics," Advanced Drug Delivery Reviews 61(6):467-477, Jun. 2009. (Author Manuscript provided, PMCID: PMC2700776, available in PMC Jun. 21, 2010, 22 pages).
Sun, C., et al., "PEG-Mediated Synthesis of Highly Dispersive Multifunctional Superparamagnetic Nanoparticles: Their Physicochemical Properties and Function In Vivo," ACS Nano 4(4):2402-2410, Apr. 2010.
Sun, S., et al., "Monodisperse $MFe_2O_4$ (M = Fe, Co, Mn) Nanoparticles," Journal of the American Cancer Society 126(1):273-279, Jan. 2004.
Szakács, G., et al., "Targeting Multidrug Resistance in Cancer," Nature Reviews: Drug Discovery 5(3):219-234, Mar. 2006.
Veiseh, O., et al., "Chlorotoxin Bound Magnetic Nanovector Tailored for Cancer Cell Targeting, Imaging, and siRNA Delivery," Biomaterials 31(31):8032-8042, Nov. 2010. (Author Manuscript provided, PMCID: PMC2930137, available in PMC Nov. 1, 2011, 21 pages).
Veiseh, O., et al., "Design and Fabrication of Magnetic Nanoparticles for Targeted Drug Delivery and Imaging," Advanced Drug Delivery Review 62(3):284-304, Mar. 2010. (Author Manuscript provided, PMCID: PMC2827645, available in PMC Mar. 8, 2011, 42 pages).
Wu, X.L., et al., "Tumor-Targeting Peptide Conjugated pH-Responsive Micelles as a Potential Drug Carrier for Cancer Therapy," Bioconjugate Chemicals 21(2):208-213, Feb. 2010.
Xie, J., et al., "Surface-Engineered Magnetic Nanoparticle Platforms for Cancer Imaging and Therapy," Accounts of Chemical Research 44(10):883-892, Oct. 2011.
Yang, J., et al., "Multifunctional Magneto-Polymeric Nanohybrids for Targeted Detection and Synergistic Therapeutic Effects on Breast Cancer," Angewandte Chemie International Edition 46(46):8836-8839, Nov. 2007.
Zou, P., et al., "Superparamagnetic Iron Oxide 'Nanotheranostics' for Targeted Cancer Cell Imaging and pH-Dependent Intracellular Drug Release," Molecular Pharmaceutics 7(6):1974-1984, Dec. 2010. (Author Manuscript provided, PMCID: PMC2997864, available in PMC Dec. 6, 2011, 23 pages).
Zugates, G.T., et al., "Synthesis of Poly(βamino ester)s With Thiol-Reactive Side Chains for DNA Delivery," Journal of the American Chemical Society 128(39):12726-12734, Oct. 2006.

* cited by examiner

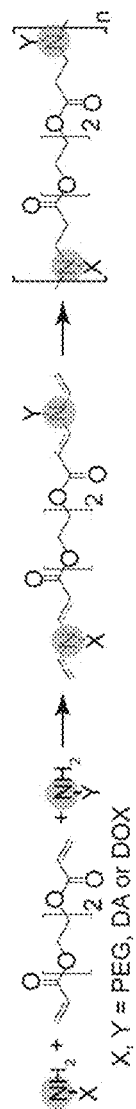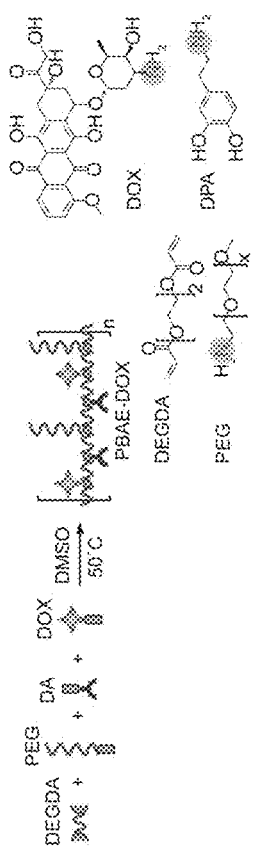
Fig. 1A.
Fig. 1B.

| Name | 24 h | 72 h |
|---|---|---|
| DOX | 0.748 ± 0.146 | 1.102 ± 0.105 |
| NP-DOX | 0.846 ± 0.050 | 0.386 ± 0.040 |
| p Value | > 0.05 | < 0.001 |

THERANOSTIC NANOPARTICLE AND METHODS FOR MAKING AND USING THE NANOPARTICLE

CROSS-REFERENCE TO RELATED APPLICATION

The present application claims the benefit of U.S. Patent Application No. 61/684,064, filed Aug. 16, 2012, expressly incorporated herein by reference in its entirety.

STATEMENT OF GOVERNMENT LICENSE RIGHTS

This invention was made with Government support under Grant Nos. R01EB006043 and R01CA134213 awarded by National Institutes of Health. The Government has certain rights in the invention.

BACKGROUND OF THE INVENTION

Cancer remains one of the most devastating diseases despite continuous development and innovation in cancer therapy. Of the current treatment options, chemotherapy remains a major component of cancer therapeutic regimens. However, the efficacy of chemotherapy is impaired by the development of the multidrug resistance (MDR) phenotype by cancer cells. MDR is characterized by the overexpression of ATP-binding cassette (ABC) transporters which increase the efflux of chemotherapeutic drugs out of cancer cells before the drug can reach its intracellular site of action. MDR inhibitors have been developed to improve the drug accumulation in cancer cells, but their widespread clinical use has been limited by high toxicity and low efficacy.

Nanoparticle-based therapeutics offers a new approach to circumvent MDR by improving the intracellular accumulation of chemotherapy drug. Furthermore, these therapeutic nanoparticles could be modified with imaging components to produce theranostic systems that enable non-invasive, real-time monitoring of drug delivery and therapeutic response. Of the theranostic nanoparticles being studied, superparamagnetic iron oxide nanoparticles (SPIONs) are appealing owing to their intrinsic superparamagnetism that provides contrast in magnetic resonance imaging (MRI), and solid core to which therapeutics can be easily arranged. Furthermore, iron oxide has been known to be biocompatible and biodegradable and a number of drug loaded theranostic SPIONs have been investigated.

Despite the promise of these theranostic nanoparticles, fabrication of reproducible and consistent formulations with controlled drug loading and release profiles remains a significant challenge and a major barrier to their clinical application. The difficulty lies in fabrication schemes that involve complex, multi-step synthesis procedures that can multiply and accumulate the variations or fluctuations from each step leading to significant batch-to-batch inconsistencies and inefficient drug loading. The present invention seeks to fulfill these needs and provides further related advantages.

SUMMARY OF THE INVENTION

The present invention provides a nanoparticle having a poly(beta-amino ester) coating that includes one or more therapeutic agents that can be delivered by the particle and one or more anchoring groups that couple the polymer to the core surface. Methods for making and using the nanoparticles are also provided.

In one aspect, the invention provides a functional nanoparticle having a poly(beta-amino ester) (PBAE) coating. In one embodiment, the nanoparticle comprises (a) a core having a surface and comprising a core material and (b) a poly(beta-amino ester) coupled to the surface of the core. The nanoparticle's poly(beta-amino ester) comprises a poly (beta-amino ester) backbone having one or more therapeutic agents and one or more anchoring groups covalently coupled thereto. In this embodiment, the poly(beta-amino ester) has the formula:

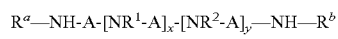

$R^a$—NH-A-[NR$^1$-A]$_x$-[NR$^2$-A]$_y$—NH—R$^b$ wherein
A has the formula —CH$_2$CH$_2$C(=O)O-L-OC(=O)CH$_2$CH$_2$—, wherein L is a group linking the ester moieties;
$R^1$ is a pendant group comprising a therapeutic agent;
$R^2$ is a pendant group comprising an anchoring group;
x is an integer from 1 to about 599;
y is an integer from 1 to about 599;
x+y is less than or equal to about 600; and
$R^a$ and $R^b$ are independently selected from $R^1$ and $R^2$.

In certain embodiments, the nanoparticle further comprises a polyalkylene oxide group pendant from the poly (beta-amino ester) backbone. In this embodiment, the poly (beta-amino ester) has the formula:

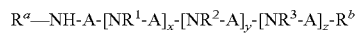

$R^a$—NH-A-[NR$^1$-A]$_x$-[NR$^2$-A]$_y$-[NR$^3$-A]$_z$-R$^b$ wherein
A, L, $R^1$, and $R^2$ are as defined above, $R^3$ is a pendant group comprising a polyalkylene oxide group; x is an integer from 1 to about 598; y is an integer from 1 to about 598; z is an integer from 1 to about 598; x+y+z is less than or equal to about 600; and $R^a$ and $R^b$ are independently selected from $R^1$, $R^2$, and $R^3$.

In certain embodiments, the nanoparticle further includes a targeting agent.

In other embodiments, the nanoparticle further includes a fluorescent agent.

In further embodiments, the nanoparticle further includes a targeting agent and a fluorescent agent.

In another aspect of the invention, a composition that includes the nanoparticle is provided. The composition includes a nanoparticle and a carrier suitable for administration to a warm-blooded subject (e.g., human).

In further aspects, the invention provides methods for using the nanoparticle.

In one embodiment, the invention provides a method for introducing a therapeutic agent into a cell comprising contacting a cell with a nanoparticle of the invention.

In another embodiment, the invention provides a method for detecting cells or tissues by magnetic resonance imaging. In the method, cells or tissues of interest are contacted with a nanoparticle of the invention and the level of binding of the nanoparticle is measured. An elevated level of binding, relative to normal cells or tissues, is indicative of binding to the cells or tissues of interest.

In a further embodiment, the invention provides a method for treating a tissue with a therapeutic agent, comprising contacting a tissue of interest with a nanoparticle of the invention.

In another aspect of the invention, a method for making a nanoparticle having a poly(beta-amino ester) coating is provided. In one embodiment, the method includes the steps:

(a) reacting one or more amine compounds having the formula $NH_2$—$R^1$ and one or more amine compounds having formula $NH_2$—$R^2$ with a compound having the formula

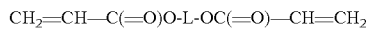

to provide a poly(beta-amino ester) having the formula

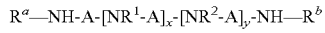

wherein

A has the formula —$CH_2CH_2C(=O)O$-L-$OC(=O)$ $CH_2CH_2$—;

L is a group linking the ester moieties;

$R^1$ is a group comprising a therapeutic agent;

$R^2$ is a group comprising an anchoring group;

x is an integer from 1 to about 599;

y is an integer from 1 to about 599;

x+y is less than or equal to about 600; and $R^a$ and $R^b$ are independently selected from $R^1$ and $R^2$; and (b) coupling the poly(beta-amino ester) to the surface of a nanoparticle having a core and a surface to provide a nanoparticle coated with a poly(beta-amino ester).

In another embodiment, the method further includes reacting one or more amine compounds having the formula $NH_2$—$R^3$ with the compound having the formula

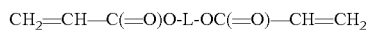

to provide a poly(beta-amino ester) having the formula

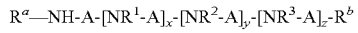

wherein $R^3$ is a group comprising a polyalkylene oxide group;

x is an integer from 1 to about 598;

y is an integer from 1 to about 598;

z is an integer from 1 to about 598;

x+y+z is less than or equal to about 600; and $R^a$ and $R^b$ are independently selected from $R^1$, $R^2$, and $R^3$.

In certain embodiments, coupling the poly(beta-amino ester) to the surface of the nanoparticle includes ligand exchange.

DESCRIPTION OF THE DRAWINGS

The patent or application file contains at least one drawing executed in color. Copies of this patent or patent application publication with color drawing(s) will be provided by the Office upon request and payment of the necessary fee The foregoing aspects and many of the attendant advantages of this invention will become more readily appreciated as the same become better understood by reference to the following detailed description, when taken in conjunction with the accompanying drawings.

FIGS. 1A-1C are schematic illustrations of the synthesis of a representative poly(beta-amino ester) (PBAE) and nanoparticle surface modification. FIG. 1A is a schematic illustration of the synthesis of a representative PBAE copolymer through Michael addition reaction with appropriate amine compounds. FIG. 1B is a schematic illustration of the synthesis of a representative chemotherapeutic-loaded poly (beta-amino ester) the invention, a PBAE-doxorubicin copolymer (PBAE-DOX) through reaction between di(ethylene glycol) diacrylate (DEGDA), methoxy-polyethylene glycol-amine (PEG), dopamine (DA), and doxorubicin (DOX). This illustration does not reflect the exact sequence and ratio of each component. FIG. 1C is a schematic illustration of the formation of a representative nanoparticle of the invention, a PBAE-doxorubicin-coated nanoparticle (NP-DOX) via ligand-exchange reaction with an oleic acid nanoparticle (NP-OA).

FIG. 2A compares DOX, PEG, and DA feeding and loading ratios for a representative PBAE polymer. Feeding and loading ratios refer to the weight ratios of each component in the reactants and product (PBAE-DOX), respectively. FIG. 2B compares absorbance and fluorescence emission spectra of DOX in the representative PBAE-DOX copolymer.

FIG. 3A are TEM images of NP-OA and NP-DOX. The scale bar: 10 nm. FIG. 3B compares hydrodynamic size of NP-DOX in cell culture media (DMEM with 10% FBS) as a function of time. FIG. 3C illustrates drug release profiles of DOX from NP-DOX in solutions of pH 4.5, pH 5.5, and pH 7.4 at 37° C.

FIG. 4A compares MR phantom images of NP-DOX at different iron concentrations. FIG. 4B compares $R_2$ magnetic relaxation of NP-DOX as a function of iron concentration.

FIG. 5A is a graphic presentation of DOX and NP-DOX at 24 h and 72 h after treatment of C6-ADR cells. FIG. 5B is a table of $IC_{50}$ values of free DOX and NP-DOX at 24 h and 72 h after treatment of C6-ADR cells (p values were determined by Student's t-test. N.S. indicates no significance, *** indicates P<0.001).

FIG. 6A compares intracellular iron quantification of C6-ADR cells at 4 h and 24 h after initial exposure to NP-DOX. FIG. 6B compares intracellular DOX quantification of C6-ADR cells at 4 h and 24 h after initial exposure to NP-DOX or free DOX. N.S. indicates no significance, ** indicates p<0.01, as determined by Student's t-test.

DETAILED DESCRIPTION OF THE INVENTION

Figure 1C:
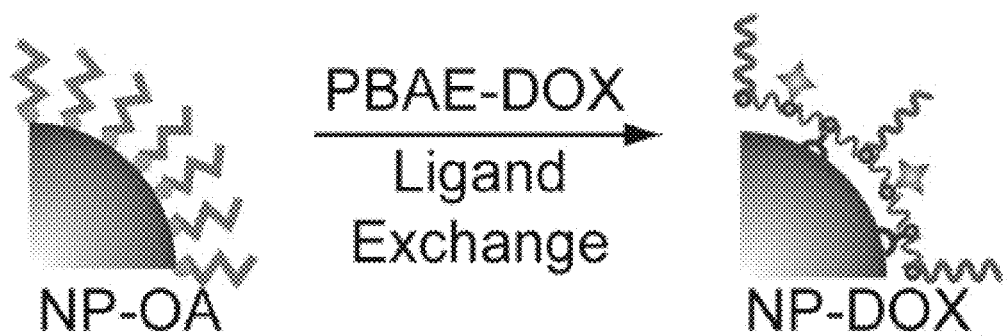

The present invention provides a nanoparticle having a poly(beta-amino ester) coating. The poly(beta-amino ester) coating includes one or more therapeutic agents that can be delivered by the particle and one or more anchoring groups that couple the polymer to the core surface. In certain embodiments, the poly(beta-amino ester) includes one or more polyalkylene oxide groups. In certain embodiments, the nanoparticle has a core that includes a material that imparts magnetic resonance imaging activity to the particle. The poly(beta-amino ester) can further include a targeting agent to target the nanoparticle to a site of interest and a diagnostic agent that allows for imaging of the particle. Methods for making and using the nanoparticles are also provided.

Nanoparticle Having Poly(Beta-Amino Ester) Coating

In one aspect, the invention provides a functional nanoparticle having a poly(beta-amino ester) (PBAE) coating. In one embodiment, the nanoparticle comprises (a) a core having a surface and comprising a core material and (b) a poly(beta-amino ester) coupled to the surface of the core. The nanoparticle's poly(beta-amino ester) comprises a poly (beta-amino ester) backbone having one or more therapeutic agents and one or more anchoring groups covalently coupled thereto. In this embodiment, the poly(beta-amino ester) has the formula:

wherein

A has the formula —$CH_2CH_2C(=O)O$-L-$OC(=O)CH_2CH_2$—, wherein L is a group linking the ester moieties;

$R^1$ is a pendant group comprising a therapeutic agent;

$R^2$ is a pendant group comprising an anchoring group;

x is an integer from 1 to about 599;

y is an integer from 1 to about 599;

x+y is less than or equal to about 600; and $R^a$ and $R^b$ are independently selected from $R^1$ and $R^2$.

As defined above, x and y refer to the number of repeating units present in the polymer. Alternatively, x and y can refer to the mole fraction of repeating units in the polymer. When referring to mole fraction, x is from about 0.01 to 0.99, y is from about 0.01 to 0.99, and x+y is 1.0

It will be appreciated that the above poly(beta-amino ester) formula is a schematic formula and denotes the polymer composition. The polymer includes repeating units $NR^1$-A (x units) and $NR^2$-A (y units). The formula does not denote polymer structure with regard to the order of the repeating units (e.g., the polymer can be a random copolymer).

In certain embodiments, the nanoparticle further comprises a polyalkylene oxide group pendant from the poly (beta-amino ester) backbone. In this embodiment, the poly (beta-amino ester) has the formula:

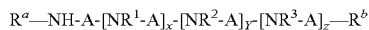

wherein

A, L, $R^1$, and $R^2$ are as defined above, $R^3$ is a pendant group comprising a polyalkylene oxide group; x is an integer from 1 to about 598; y is an integer from 1 to about 598; z is an integer from 1 to about 598; x+y+z is less than or equal to about 600; and $R^a$ and $R^b$ are independently selected from $R^1$, $R^2$, and $R^3$.

In certain embodiments, the polyalkylene oxide group is a polyethylene oxide group.

For the above embodiment, x, y, and z refer to the number of repeating units present in the polymer. Alternatively, x and y can refer to the mole fraction of repeating units in the polymer. When referring to mole fraction, x is from about 0.01 to 0.98, y is from about 0.01 to 0.98, z is from about 0.01 to 0.98, and x+y+z is 1.0.

It will be appreciated that the above poly(beta-amino ester) formula is a schematic formula and denotes the polymer composition. The polymer includes repeating units $NR^1$-A (x units), $NR^2$-A (y units), and $NR^3$-A (z units). The formula does not denote polymer structure with regard to the order of the repeating units (e.g., the polymer can be a random copolymer).

In certain embodiments, the ratio of x:y is about 1:2. In other embodiments, x:y is about 1:3. In further embodiments, x:y is about 1:1.

For embodiments that further include $R^3$, the ratio of x:y:z is about 1:2:2 in certain embodiments. In other embodiments, x:y:z is about 1:3:3. In further embodiments, x:y:z is about 1:1:1.

The poly(beta-amino ester) includes pendant groups $R^1$, $R^2$, and $R^3$ that are covalently coupled to the poly(beta-amino ester) backbone. These pendant groups are introduced into the polymer as amine compounds (i.e., $NH_2R^1$, $NH_2R^2$, and $NH_2R^3$) during the polymerization process. See FIGS. 1A and 1B. It will be appreciated that the pendant groups comprising the therapeutic agent, anchoring agent, and polyalkylene oxide groups can be derived from therapeutic agents, anchoring agents, and polyalkylene oxide groups that include amine groups (i.e., —$NH_2$) that are native to the therapeutic agent, anchoring agent, and polyalkylene oxide groups. Alternatively, it will be appreciated that the pendant groups comprising the therapeutic agent, anchoring agent, and polyalkylene oxide groups can be derived from therapeutic agents, anchoring agents, and polyalkylene oxide groups that have been modified to include an amine group (i.e., —$NH_2$) so as to facilitate their incorporation into the poly(beta-amino ester) during polymerization. Methods for modifying groups therapeutic agents, anchoring agents, and polyalkylene oxide groups to include an amine group are well known to those of skill in the art and can be accomplished by traditional synthetic chemical reactions.

For the poly(beta-amino esters) described above, L is a group linking the ester moieties. Suitable linking group L includes from 2 to about 20 carbon atoms optionally including one or more heteroatoms selected from nitrogen, oxygen, silicon, phosphorous, sulfur. Linking group L may optionally be substituted with one or more groups selected from C1-C6 alkyl, C2-C6 alkenyl, C2-C6 alkynyl, amino, C1-C6 alkyl amino, C1-C6 dialkylamino, C1-C6 trialkylamino, hydroxyl, C1-C6 alkoxyl, halogen (e.g., fluoro, chloro, bromo, iodo), aryl, heterocyclic, aromatic heterocyclic, cyano, amide, carbamoyl, carboxyl, carboxyl ester, thioether, alkylthioether, and thiol. Representative linking groups L include those described in WO 2004/106411 (groups B), expressly incorporated herein by reference in its entirety. In one embodiment, L is —$(CH_2CH_2O)_n CH_2CH_2$—, where n is an integer from 1 to about 50, preferably from 1 to 10. In one embodiment, L is —$CH_2CH_2OCH_2CH_2$—. In another embodiment, L is —$(CH_2)_n$—, where n is an integer from 2 to about 20, preferably from 2 to 10.

In certain embodiments, wherein the poly(beta-amino ester) has an average molecular weight from about 3000 to about 300,000 g/mole. In one embodiment, the poly(beta-amino ester) has an average molecular weight from about 10,000 to about 50,000 g/mole. In another embodiment, the poly(beta-amino ester) has an average molecular weight from about 25,000 to about 75,000 g/mole.

As used herein, the term "coating" refers to the poly(beta-amino ester) coupled to the surface of the nanoparticle core. In certain embodiments, the core is substantially surrounded by poly(beta-amino ester) (i.e., the core is coated with the poly(beta-amino ester)). The poly(beta-amino ester) is directly coupled to the core surface through the polymer's anchoring groups. In certain embodiments, the poly(beta-amino ester) is covalently coupled to the core surface. In others embodiments, the poly(beta-amino ester) is coupled to the core surface by non-covalent coupling (e.g., electrostatic interaction, ionic association). The poly(beta-amino ester) is directly coupled to the core surface. The poly(beta-amino ester) is not coupled to the core surface through one or more other materials (e.g., a protein, peptide, or nucleic acid such as a DNA or an RNA). In the nanoparticle of the invention, there are no layers intermediate the core surface and the poly(beta-amino ester).

Suitable anchoring groups include carboxylic acid groups, hydroxamic acid groups, phosphonic acid groups, and hydroxybenzene groups. In certain embodiments, the anchoring group is a dihydroxybenzene group such as a 1,2-dihydroxybenzene group. In one embodiment, the anchoring group is a 4-(2-aminoethyl)benzene-1,2-diol group (i.e., catecholamine or dopamine).

The phrase "core having a surface and comprising a core material" refers to a solid nanoparticle. The nanoparticle core is not hollow (e.g., not a solid shell encapsulating a void). The core material can impart functional properties to the nanoparticle (e.g., magnetic properties). The core material is not a polymeric material (e.g., the nanoparticle is not a polymer nanoparticle or a polymeric nanosphere). As used herein the term "polymeric material" refers to an organic polymer material (e.g., poly(glycidyl methacrylate), poly (styrene), poly(alkylacrylate)). The core's surface defines the core's outermost surface. In certain embodiments, the nanoparticle core is a solid core comprising a material having magnetic resonance imaging activity (e.g., iron oxide).

The nanoparticle includes a core material. For magnetic resonance imaging applications, the core material is a material having magnetic resonance imaging activity (e.g., the material is paramagnetic). In certain embodiments, the core material is a magnetic material. In other embodiments, the core material is a semiconductor material. Representative core materials include ferrous oxide, ferric oxide, silicon oxide, polycrystalline silicon oxide, silicon nitride, aluminum oxide, germanium oxide, zinc selenide, tin dioxide, titanium, titanium dioxide, nickel titanium, indium tin oxide, gadolinium oxide, stainless steel, gold, and mixtures thereof.

The particle of the invention has nanoscale dimensions. Suitable particles have a physical size less than about 30 nm. In certain embodiments, the nanoparticles have a physical size from about 10 to about 30 nm. In other embodiments, the nanoparticles have a physical size from about 10 to about 20 nm. As used herein, the term "physical size" refers the overall diameter of the nanoparticle, including core (as determined by TEM) and coating thickness. Suitable particles have a mean core size of from about 2 to about 25 nm. In certain embodiments, the nanoparticles have a mean core size of about 7 nm. As used herein, the term "mean core size" refers to the core size determined by TEM. Suitable particles have a hydrodynamic size less than about 150 nm. In certain embodiments, the nanoparticles have a hydrodynamic size from about 50 to about 150 nm. In certain embodiments, the nanoparticles have a hydrodynamic size of about 80 nm. As used herein, the term "hydrodynamic size" refers the radius of a hard sphere that diffuses at the same rate as the particle under examination as measured by DLS. The hydrodynamic radius is calculated using the particle diffusion coefficient and the Stokes-Einstein equation given below, where k is the Boltzmann constant, T is the temperature, and η is the dispersant viscosity:

$$R_B = \frac{kT}{6\pi\eta D}.$$

A single exponential or Cumulant fit of the correlation curve is the fitting procedure recommended by the International Standards Organization (ISO). The hydrodynamic size extracted using this method is an intensity weighted average called the Z average.

Therapeutic Agents.

As used herein the term "therapeutic agent" includes any agent that elicits a cyctotoxic, cytosytic, or immunomodulant effect on cells. Therapeutic agents include chemotherapeutic agents, gene therapeutic agents, therapeutic radioisotopes, and combinations thereof.

Therapeutic agents effectively delivered by the nanoparticles of the invention include small organic molecules, peptides, aptamers, proteins, and nucleic acids. In certain embodiments, the therapeutic agent include antibodies and functional fragments thereof, fusion proteins, and immunomodulant agents. In other embodiments, the therapeutic agent is an RNA or a DNA (e.g., an siRNA).

Suitable therapeutic agents include conventional therapeutic agents, such as small molecules; biotherapeutic agents, such as peptides, proteins, and nucleic acids (e.g., DNA, RNA, cDNA, siRNA); and cytotoxic agents, such as alkylating agents, purine antagonists, pyrimidine antagonists, plant alkaloids, intercalating antibiotics, antitumor antibiotics (e.g., trastuzumab), binding epidermal growth factor receptors (tyrosine-kinase inhibitors), histone deacetylase inhibitor, aromatase inhibitors, anti-metabolites (e.g., folic acid analogs, methotrexate, 5-fluoruracil), mitotic inhibitors (e.g., taxol, paclitaxel, docetaxel), growth factor inhibitors, cell cycle inhibitors, enzymes, topoisomerase inhibitors, biological response modifiers, anti-hormones, anti-androgens, and various cytokines for immunotherapy. Representative cytotoxic agents include BCNU, cisplatin, gemcitabine, hydroxyurea, paclitaxel, temozomide, topotecan, fluorouracil, vincristine, vinblastine, procarbazine, dacarbazine, altretamine, cisplatin, methotrexate, mercaptopurine, thioguanine, fludarabine phosphate, cladribine, pentostatin, fluorouracil, cytarabine, azacitidine, vinblastine, vincristine, etoposide, teniposide, irinotecan, docetaxel, doxorubicin, daunorubicin, dactinomycin, idarubicin, plicamycin, mitomycin, bortezomib, bleomycin, tamoxifen, flutamide, leuprolide, goserelin, aminoglutethimide, anastrozole, amsacrine, asparaginase, mitoxantrone, mitotane, and amifostine.

Suitable therapeutic drugs include siRNAs and antitumor tumor drugs than function in cytoplasm.

The therapeutic agent is covalently coupled to the poly (beta-amino ester). In certain embodiments, the therapeutic agent is covalently coupled through a cleavable linkage. Suitable cleavable linkages include linkages cleavable under acidic conditions such as in the acidic microenvironment of cancer cell (e.g., pH less than physiological pH, from about 4.0 to about 6.8. Representative cleavable linkages include disulfide, acetal, hydrazone, carbamates, ester, orthoester, and thioester linkages.

In certain embodiments, the nanoparticles of the invention further include one or more other agents. Thus, in other embodiments, the nanoparticles of the invention further include one or more of a targeting agent to target the nanoparticle to a site of interest, or a diagnostic agent that allows for imaging of the particle.

Targeting Agents.

Suitable targeting agents include compounds and molecules that direct the nanoparticle to the site of interest. Suitable targeting agents include tumor targeting agents such as ligands that specifically bind to tumor cell surface receptors.

Representative targeting agents include small molecules, peptides, proteins (e.g., fusion protein, antibody or functional fragment thereof), aptamers, and nucleic acids. Representative small molecule targeting agents include biotin, folic acid, and methotrexate (folate receptors), non-peptidic RGD mimetics, vitamins, and hormones. Representative peptide targeting agents include RGD (avβ3 integrin), chlorotoxin (MMP2), and VHPNKK (endothelial vascular adhesion molecules). Representative protein targeting agents include antibodies against the surface receptors of tumor cells, such as monoclonal antibody A7 (colorectal carcinoma), herceptin (Her2/ner), rituxan (CD20 antigen), IF5 (anti-CD20), and CC49 (anti-TAG-72), and ligands such as annexin V (phosphatidylserine) and transferrin (transferrin receptor). Representative aptamer targeting agents include A10 RNA apatamer (prostate-specific membrane antigen) and Thrm-A and Thrm-B DNA aptamers (human alpha-thrombin protein). Targets for the agents noted above are in parentheses. Representative nucleic acid targeting agents include DNAs (e.g., cDNA) and RNAs (e.g., siRNA).

In one embodiment, the invention provides a nanoparticle, comprising:

(a) a core comprising a magnetic material and having a surface;

(b) a poly(beta-amino ester) coupled to the surface of the core, wherein the poly(beta-amino ester) comprises a poly(beta-amino ester) backbone having one or more therapeutic agents and one or more anchoring groups covalently coupled thereto; and (c) a targeting agent.

In another embodiment, the nanoparticle further comprises a polyalkylene oxide group (e.g., polyethylene oxide) pendant from the poly(beta-amino ester).

For this embodiment, suitable therapeutic agents, anchoring agents, targeting agents, and polyalkylene oxide groups are as described above.

Diagnostic Agents.

Suitable diagnostic agents include optical agents, such as fluorescent agents that emit light in the visible and near-infrared (e.g., fluorescein and cyanine derivatives). Suitable fluorescent agents include fluorescein and derivatives, rhodamine and derivatives, and cyanines. Representative fluorescent agents include fluorescein, OREGON GREEN 488, ALEXA FLUOR 555, ALEXA FLUOR 647, ALEXA FLUOR 680, Cy5, Cy5.5, and Cy7.

In one embodiment, the invention provides a nanoparticle, comprising:

(a) a core comprising a magnetic material and having a surface;

(b) a poly(beta-amino ester) coupled to the surface of the core, wherein the poly(beta-amino ester) comprises a poly(beta-amino ester) backbone having one or more therapeutic agents and one or more anchoring groups covalently coupled thereto; and (c) a diagnostic agent.

In another embodiment, the invention provides a nanoparticle, comprising:

(a) a core comprising a magnetic material and having a surface;

(b) a poly(beta-amino ester) coupled to the surface of the core, wherein the poly(beta-amino ester) comprises a poly(beta-amino ester) backbone having one or more therapeutic agents and one or more anchoring groups covalently coupled thereto;

(c) a diagnostic agent; and (d) a targeting agent.

In other embodiments, the above nanoparticles further comprise a polyalkylene oxide group (e.g., polyethylene oxide) pendant from the poly(beta-amino ester).

For these embodiments, suitable therapeutic agents, anchoring agents, targeting agents, diagnostic agents, and polyalkylene oxide groups are as described above.

The preparation of representative nanoparticles of the invention is described in Example 1 and illustrated schematically in FIGS. 1A-1C.

In another aspect of the invention, a composition is provided that includes a nanoparticle of the invention and a carrier suitable for administration to a warm-blooded subject (e.g., a human subject). Suitable carriers include those suitable for intravenous injection (e.g., saline or dextrose).

Methods for Using Nanoparticles Having Poly(Beta-Amino Ester) Coating

In other aspects, the invention provides methods for using the nanoparticles of the invention.

In certain embodiments, the invention provides methods for introducing a material (e.g., therapeutic and/or diagnostic agent) to a cell. In other embodiments, the invention provides imaging methods such as magnetic resonance imaging when the core has magnetic resonance activity, and optical imaging when the nanoparticle includes a fluorescent agent. As noted above, the nanoparticles of the invention can also be used for drug delivery when the nanoparticle includes a therapeutic agent. For nanoparticles of the invention that include targeting agents, imaging of and drug delivery to target sites of interest are provided.

In one embodiment, the method for introducing a therapeutic agent into a cell comprises contacting a cell with a nanoparticle of the invention.

In another embodiment, the invention provides a method for silencing or reducing the expression level of a gene. In the method, a cell of interest is contacted with a nanoparticle of the invention in which the nanoparticle comprises a suitable siRNA (i.e., therapeutic agent) effective to silence or reduce the expression level of the particular gene.

In a further embodiment, the invention provides a method for detecting (or imaging) cells or tissues by magnetic resonance imaging, comprising:

(a) contacting cells or tissues of interest with a nanoparticle of the invention having affinity and specificity for the cells or tissues of interest, wherein the nanoparticle comprises (i) a core comprising a magnetic material and having a surface, (ii) a poly(beta-amino ester) coupled to the surface of the core, wherein the poly(beta-amino ester) comprises a poly(beta-amino ester) backbone having one or more therapeutic agents and one or more anchoring groups covalently coupled thereto, and (iii) optionally a targeting agent, wherein the targeting agent has an affinity and specificity to the cells or tissues of interest; and (b) measuring the level of binding of the nanoparticle to the cells or tissues of interest, wherein an elevated level of binding, relative to normal cells or tissues, is indicative of binding to the cells or tissues of interest.

In the method, the level of binding is measured by magnetic resonance imaging techniques. In a further embodiment of the above method, the nanoparticle further includes a fluorescent agent. In this embodiment, the level of binding can be measured by magnetic resonance and/or fluorescence imaging techniques. The methods are applicable to detecting or imaging cells or tissues in vitro. The methods are also applicable to detecting or imaging cells or tissues in vivo. In this embodiment, the nanoparticles are administered to a subject (e.g., warm-blooded animal) by, for example, intravenous injection.

In another embodiment, the invention provides a method for treating a tissue, comprising contacting a tissue of interest with a nanoparticle of the invention having affinity and specificity for the tissue of interest, wherein the nanoparticle comprises (a) a core comprising a core material and having a surface, (b) a poly(beta-amino ester) coupled to the surface of the core, wherein the poly(beta-amino ester) comprises a poly(beta-amino ester) backbone having one or more therapeutic agents and one or more anchoring groups covalently coupled thereto, and (c) optionally a targeting agent, wherein the targeting agent has an affinity and specificity to the cells or tissues of interest.

The methods are also applicable to treating tissues in vivo. In this embodiment, the nanoparticles are administered to a subject (e.g., warm-blooded animal) by, for example, intravenous injection.

Methods for Making Nanoparticles Having Poly(Beta-Amino Ester) Coating

In other aspects, the invention provides methods for making the nanoparticles of the invention. In one embodiment, the method comprises:

(a) reacting one or more amine compounds having the formula $NH_2$—$R^1$ and one or more amine compounds having formula $NH_2$—$R^2$ with a compound having the formula $CH_2$=$CH$—$C$(=$O$)$O$-$L$-$OC$(=$O$)—$CH$=$CH_2$ to provide a poly(beta-amino ester) having the formula

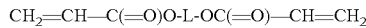

$R^a$—NH-A-$[NR^1$-A$]_x$-$[NR^2$-A$]_y$-NH—$R^b$ wherein A, L, $R^1$, $R^2$, x, y, x+y, $R^a$, and $R^b$ are as described above; and (b) coupling the poly(beta-amino ester) to the surface of a nanoparticle having a core and a surface to provide a nanoparticle coated with a poly(beta-amino ester).

In another embodiment, the method further comprises reacting one or more amine compounds having the formula $NH_2$—$R^3$ with the compound having the formula $CH_2$=$CH$—$C$(=$O$)$O$-$L$-$OC$(=$O$)—$CH$=$CH_2$ to provide a poly(beta-amino ester) having the formula

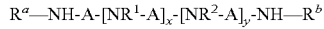

$R^a$—NH-A-$[NR^1$-A$]_x$-$[NR^2$-A$]_y$-$[NR^3$-A$]_z$-$R^b$ wherein A, L, $R^1$, $R^2$, $R^3$, x, y, z, x+y+z, $R^a$, and $R^b$ are as described above.

In certain embodiments, coupling the poly(beta-amino ester) to the surface of the nanoparticle comprises ligand exchange.

The following is a description of specific nanoparticles of the invention and methods for making and using the nanoparticles.

The present invention provides a simple and highly reproducible approach to fabricate theranostic nanoparticles that can provide efficient drug loading, controllable drug release, and imaging capability. The major components of this theranostic nanoparticle formulation include a biodegradable and pH-sensitive poly(beta-amino ester) (PBAE) copolymer, the chemotherapeutic agent doxorubicin (DOX), and a SPION core. PBAE is a class of polymers containing both pH-responsive tertiary amines and biodegradable ester groups along the backbone. DOX has been thoroughly investigated and received regulatory approval for the treatment of a variety of solid tumors and hematological cancers. Unlike conventional methods by which multiple coating components are individually assembled onto nanoparticle through multiple reaction steps and thus the control of the component ratios and optimization of drug loading is difficult, in the practice of the present invention multiple components including DOX, dopamine (DA) for anchoring on iron oxide surfaces and poly (ethylene glycol) (PEG) for improving aqueous stability and reducing protein fouling directly assemble onto PBAE backbone. The PBAE polymer system is then assembled on SPIONs using a highly efficient and controllable chemical scheme to produce DOX-loaded nanoparticles (NP-DOX).

NP-DOX and free DOX were applied to a drug-resistant C6 cell line (C6-ADR) to evaluate the feasibility of NP-DOX for overcoming MDR. The DOX dose required for NP-DOX or free DOX to reduce cell viability 50% (IC50) was determined by the Alamar Blue cell viability assay. The cellular internalization of nanoparticles was evaluated by iron quantification (Ferrozine assay), DOX quantification, as well as fluorescent microscopy.

Synthesis and Characterization of PBAE-DOX and PBAE-Polymer.

The synthesis scheme used to prepare a representative poly(beta-amino ester) (PBAE-DOX and PBAE polymer) is shown in FIG. 1. PBAE is synthesized through a reaction between bifunctional amines and diacrylate monomers (FIG. 1A). Michael addition reaction results in covalent linkages between alkene groups of diacrylate and nitrogen atoms on bifunctional amine compounds. The reaction produces tertiary amine groups and ester linkages along the backbone of PBAE. The copolymer contains four basic units: DEGDA as the backbone unit, DA as the metal binding unit, PEG as the hydrophilic unit, and DOX as the anticancer drug unit (FIG. 1B).

Figure 2A:
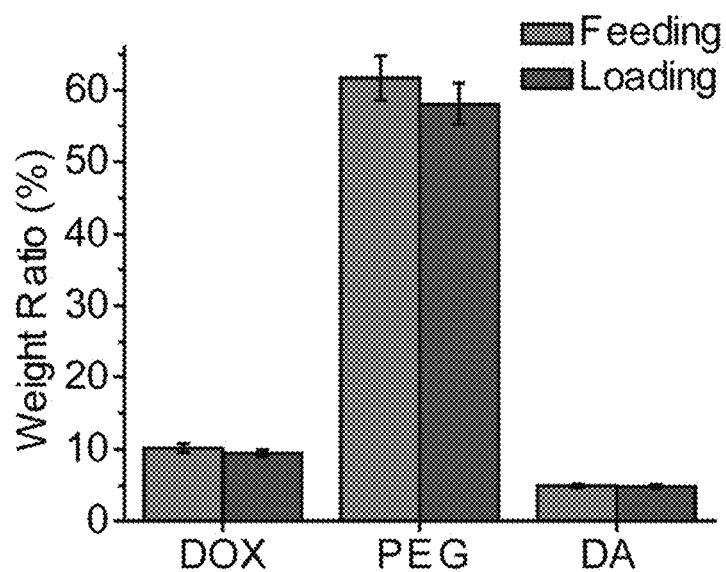
FIGS. 2A and 2B illustrate properties of PBAE copolymers.

PBAE-DOX was characterized by $^1$H-NMR spectroscopy and displayed the distinct PEG peak at δ=3.65 ppm, which was clearly resolved, and peaks at δ=6.7 and 6.5 associated with the anthracycline DOX and DA, respectively. The weight ratios of PEG, DOX, and DA in PBAE were determined by integration of the associated areas under $^1$H-NMR spectrum curve. The feeding and loading ratios refer to the polymer component weight ratios before and after polymerization, respectively (see FIG. 2A). PBAE-DOX was also characterized by UV-vis and fluorescence spectroscopy to ensure preservation of DOX fluorescence properties and to further confirm and quantify the DOX loading. Free DOX emits red fluorescence at 590 nm and the spectrum shown in FIG. 2B confirms that PBAE-DOX conserved the fluorescent property of DOX with the absorbance maxima at 485 nm and emission maxima at 590 nm. The fluorescent property of PBAE-DOX was utilized in subsequent cellular imaging to reveal the intracellular distribution of NP-DOX. Using the absorbance measured from PBAE-DOX, the weight of DOX was determined to account for 9.5% of the total PBAE weight (see Table 1).

TABLE 1

Physicochemical properties of PBAE polymers.

| PBAE | Molar ratio (DEGBA:PEG:DA:DOX) | Drug loading (%) | PEG content (%) | Yield (%) |
|---|---|---|---|---|
| PBAE-DOX | 50:19:19:12 | 9.5 | 58.1 | 42 |
| PBAE-C | 50:25:25:0 | 0.0 | 65.1 | 69 |

The synthesis of PBAE-DOX is a single-step procedure where monomers are directly mixed with a minimum amount of solvent. The end product is easily separated by precipitation with organic solvents (such as ether, hexane) and purified by size-exclusion chromatography (SEC). Because DOX, PEG, and DA all contain primary amine groups, they can be directly incorporated into the backbone of PBAE (FIG. 1A). Thus, this method eliminates the need of multiple conjugation steps used in a conventional method where each component is individually attached to polymer coating and the amount of each component can be limited and difficult to control.

The 9.5% drug-loading in PBAE-DOX is comparable to other drug delivery systems. The small difference between the feeding and loading of drug molecules (<7%, FIG. 2A) indicates high efficient conversion of free drug to conjugated drug during the polymerization reaction. Precise control of drug/polymer composition can be achieved by controlling the feeding ratio of monomers.

Synthesis and Characterization of Doxorubicin-Loaded Nanoparticles (NP-DOX).

Figure 3A:
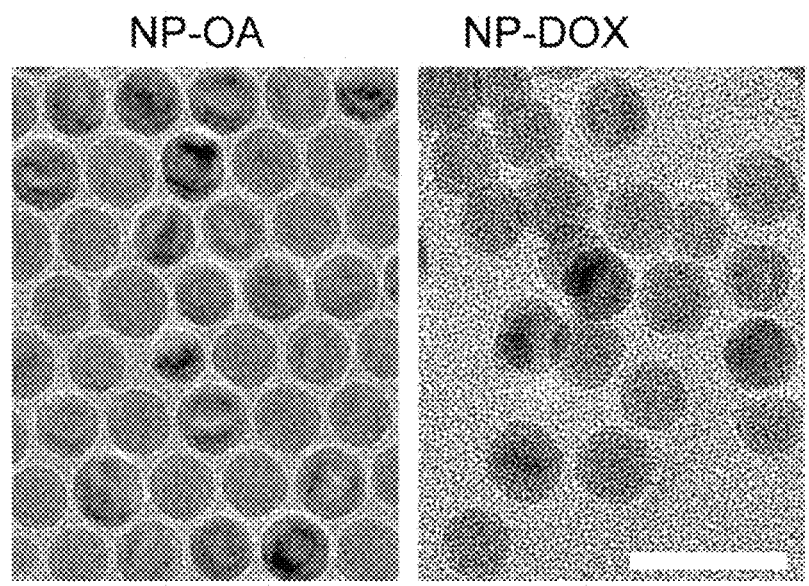
FIGS. 3A-3C illustrate physicochemical properties of a representative nanoparticle of the invention, NP-DOX.

TEM images (FIG. 3A) showed that the nanoparticles were highly dispersed before the ligand exchange process (NP-OA) and remained well dispersed and free of aggregation after ligand exchange (NP-DOX). Light scattering measurements indicated that the hydrodynamic size of NP-DOX in PBS was about 136 nm and the zeta potential at pH 7.4 was −0.7 mV, close to neutral (Table 2).

TABLE 2

Physicochemical properties of NP-DOX.

| Name | Size in PBS (nm) | Zeta potential at pH 7.4 (mV) | Polymer loading (µg/mg Fe) | Drug loading (µg/mg Fe) |
|---|---|---|---|---|
| NP-DOX | 80.5 ± 38.3[a] | −0.3 ± 3.9[b] | 7147 ± 651[c] | 679 ± 40[c] |

[a]PDI width;
[b]Zeta potential deviation;
[c]Standard deviation

The NP-DOX conjugate is formed through a ligand exchange reaction, where the oleic acid molecules on the surface of NP-OA are replaced by PBAE-DOX molecules (FIG. 1C). The DA units of PBAE-DOX contain ortho-dihydroxyphenyl groups, which form strong and stable bonds with metal oxide surfaces. The ligand exchange process is performed in organic solvents under a nitrogen atmosphere to prevent oxidation of the dopamine unit.

Figure 2B:
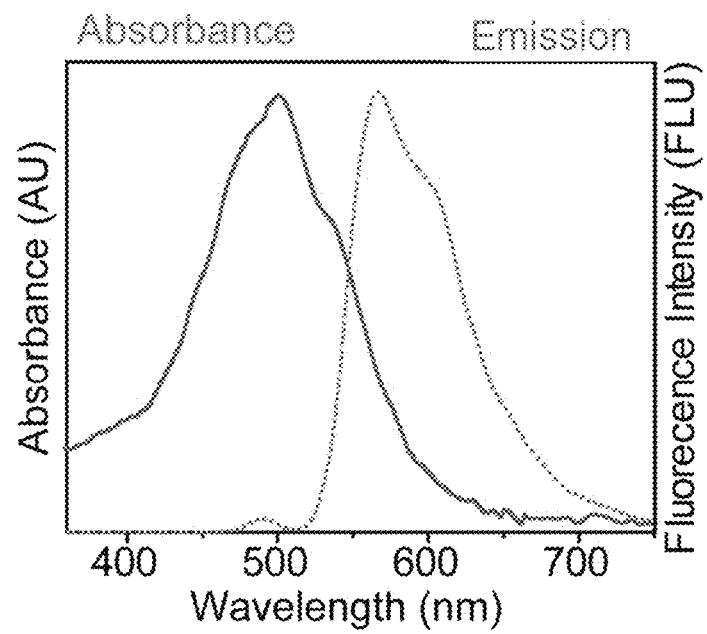

Success of the ligand exchange reaction in synthesis of NP-DOX was confirmed by $^1$H-NMR spectra of dissolved NP-DOX. NMR spectra clearly resolved the characteristic PEG ethylene peak at δ=3.65 ppm, consistent with PEG peak in the PBAE-DOX copolymer. Peaks associated with DOX were not resolved in the spectra due to low sample concentration that is required to reduce peak broadening caused by iron in solution. DOX loading of NP-DOX was found to be 679 µg/mg iron as quantified by UV-vis (FIG. 2B).

The hydrodynamic size of NP-DOX in DMEM/10% FBS was further monitored over time. Except for the initial slight increase in size, no changes in size, visible cloudiness or precipitates were observed for up to a week (FIG. 3A), indicating the NPs retained good stability. The initial size increase can be attributed to the adsorption of serum proteins on NPs.

Figure 3B:
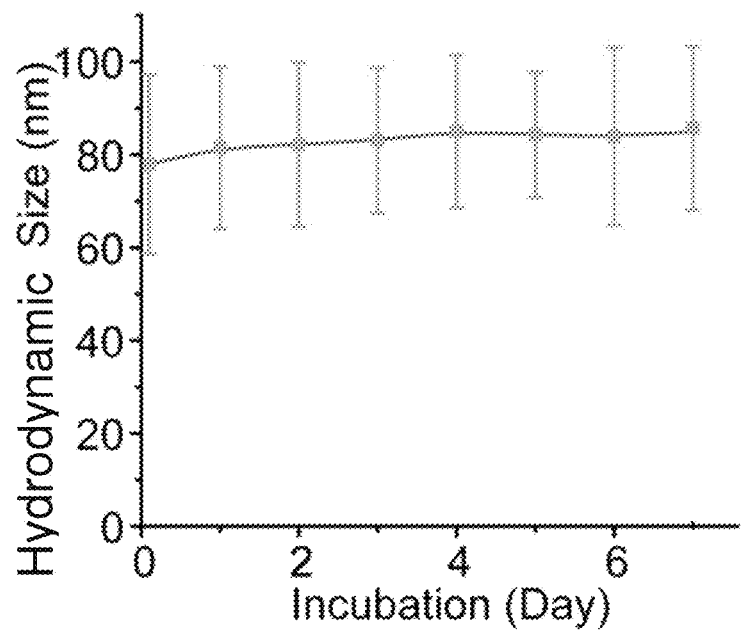

In vivo applications mandate that nanoparticle-based therapeutics should have a desirable range of hydrodynamic size and surface charge. Nanoparticles are required to be in a narrow size range to avoid elimination by kidneys (<10 nm) and minimizes liver and spleen uptake (>200 nm). Additionally, nanoparticles must maintain their stability in the presence of salts and biomacromolecules at elevated concentrations to prevent embolism and phagocytosis. The hydrodynamic sizes of NP-DOX are about 136 nm, and the zeta potential is near neutral at physiological pH. The stability of NP-DOX in culture media (FIG. 3B) can be attributed to the presence of PEG in the nanoparticle surface coating and near-neutral zeta potential. Not only are PEG molecules very hydrophilic, but they also form coiled conformations in aqueous solutions, providing excellent steric stabilization. Additionally, the anti-fouling property of surface-bound PEG molecules can alleviate opsonization of serum protein, and thus, could reduce liver and macrophage uptake when used in vivo.

Figure 3C:
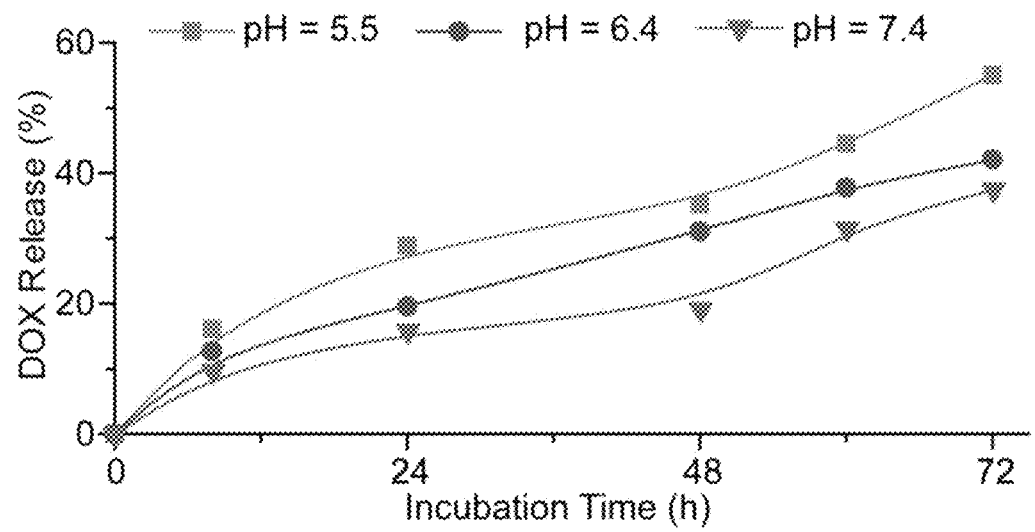

To determine the kinetics of drug release from NP-DOX, the nanoparticles were incubated in aqueous buffers to induce the degradation of PBAE polymers and liberation of drug. The drug release experiments were performed at pH 4.5, pH 5.5 and pH 7.4 at 37° C. The pH values were selected to represent the pHs of blood (pH 7.4) and endosomes/lysosomes (pH 4-6). The results showed that less than 10% of DOX was released at pH 7.4 in the first 24 h, and just over 30% of DOX was released after 72 h (FIG. 3C). At lower pH (5.5), a significantly higher amount of the drug was released in the same time period with nearly 15% of DOX released in the first 24 h, and over 55% in 72 h. At lysosomal pH (4.5), the drug release further increased: 20% at 24 h, and 60% at 72 h.

The drug loading efficiency and release kinetics are both important for the success of a drug delivery system. The drug loading of NP-DOX is directly correlated with the amount of drug in PBAE-DOX. This allows for precise control of the final component ratio of the nanoparticle coating by simply using PBAE-DOX with predetermined component ratios. High drug loading is preferable since it would reduce the dosage of pharmaceutically inactive ingredients, minimizing unintended toxicity and improving the safety profile of nanoparticle-based therapeutics. Systemic fast release kinetics can be detrimental to effective therapeutic treatment since premature drug release in the circulatory system could cause off-target accumulation resulting in unwanted toxicity. Furthermore, drug liberated before cellular internalization (i.e., extracellular drug release) would enter the target cells by passive diffusion similar to free drug, severely reducing the overall efficacy due to the MDR effects of target cells. The drug release study showed that NP-DOX releases DOX at a fairly slow rate at physiological pH, which would allow sufficient time for NP-DOX to reach the tumor site and be internalized by tumor cells, without releasing DOX prematurely. At low pH, the release rate of DOX increases, suggesting that drug release would be greatly accelerated after NP-DOX are endocytosed by cancer cells where a lower pH environment in endosomes or lysosomes enhances the cleavage of ester bonds. The results also suggests that a fraction of drug could not be released even after 72 h of incubation, possibly due to strong interactions with the surface of the iron oxide core or PBAE carrier polymer.

MR Imaging.

Figure 4A:
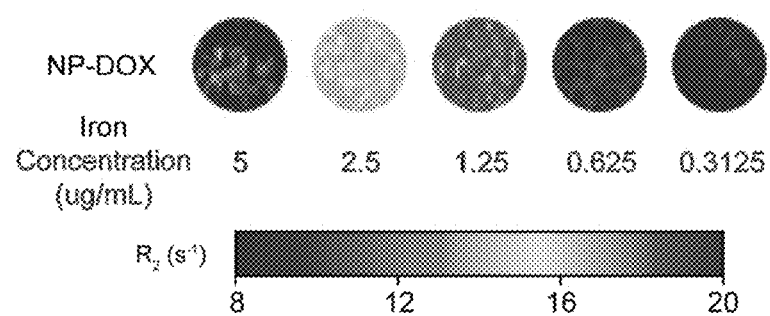
FIGS. 4A and 4B illustrate magnetic properties of a representative nanoparticle of the invention, NP-DOX.
Figure 4B:
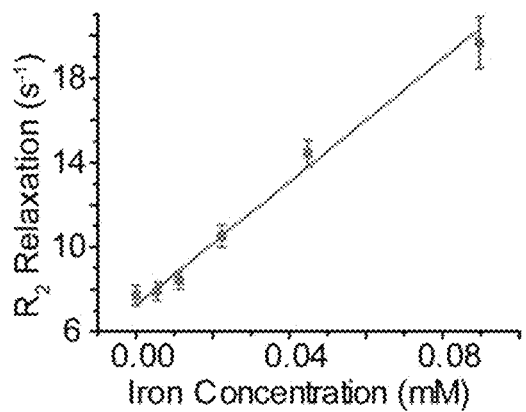

The MR relaxivity of NP-DOX was determined by MR imaging of nanoparticles dispersed in agarose gel (FIG. 4A). The NP-DOX showed $T_2$ contrast enhancement under a $T_2$-weighed imaging sequence and $r_2$ relaxivity of 146 $mM^{-1} \cdot s^{-1}$ (the slope of the relaxation vs. iron concentration curve). This $r_2$ relaxivity was similar to nanoparticle systems with a comparable iron oxide core diameter.

The ability to monitor drug delivery non-invasively and with high sensitivity is a desirable property of theranostic nanoparticles. The $r_2$ relaxivity of NP-DOX is similar to the nanoparticle system with a comparable iron oxide core diameter. Because MRI is non-invasive and is not limited by the depth of the signal source, NP-DOX can be utilized for real time drug delivery tracking and non-invasive treatment response assessment.

Dose-Response Results.

Figures 5A, 5B:
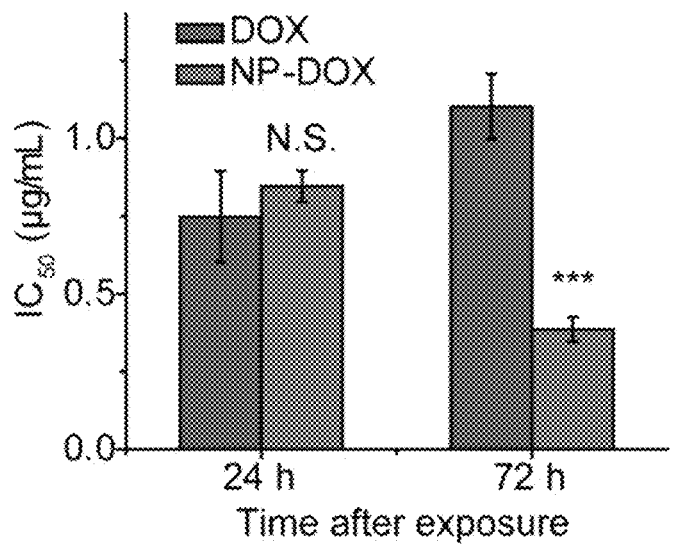
FIGS. 5A and 5B compare $IC_{50}$ values (in μg/mL) of free DOX and NP-DOX.

To examine the cytotoxic effect of nanoparticles in drug-resistant cell populations, C6-ADR cells were treated with either free DOX or NP-DOX, and the viability of treated cells was determined by the Alamar blue assay at 24 and 72 h after treatment (FIGS. 5A and 5B). At the 24 h time point, NP-DOX showed a concentration of 0.846±0.050 µg/mL that is required to induce cell death in half of the population ($IC_{50}$), comparable to free DOX (0.748±0.146 µg/mL), with no significant statistical difference, indicating comparable cytotoxicity. At the 72 h time point, NP-DOX showed a significantly lower $IC_{50}$ (0.386±0.04 µg/mL) than free DOX (1.102±0.105 µg/mL), indicating higher efficacy against C6-ADR. To verify that cytotoxicity was caused by DOX not by other nanoparticle components, control nanoparticles that were coated with copolymer only (PBAE-C, without DOX) were evaluated. The control nanoparticles did not cause any cytotoxicity up to 100 µg/mL of iron.

In drug-resistant cells like C6-ADR, intracellular free drug molecules can be removed from cytosol to extracellular space by ABC-mediated drug efflux. This process greatly lowers the effective intracellular drug concentration and reduces the efficacy of free drug in drug-resistant cells. Conversely, nanoparticle-based drug delivery vehicles could circumvent ABC-mediated drug efflux mechanism by maintaining a sustained intracellular drug concentration that is sufficient to damage target organelles. The results showed superiority of NP-DOX over free DOX in overcoming the efflux by C6-ADR cells. At 24 hrs after treatment, the $IC_{50}$ of free DOX and NP-DOX for C6-ADR cells are similar, likely due to the slow release kinetics of NP-DOX. Therefore, significant cell kill over what can be achieved by free DOX was not observed. Conversely, after 72 hrs, the nanoparticles-drug conjugate achieved significantly better efficacy (65% reduction of $IC_{50}$) than the free drug in drug-resistant cells (FIGS. 5A and 5B). This suggests that the drug release profile of NP-DOX is able to maintain a higher intracellular DOX concentration for improved and prolonged cell kill Cellular Internalization of Nanoparticles.

To study the mechanism behind the improved therapeutic efficacy against C6-ADR cells demonstrated by NP-DOX, the accumulation of NP-DOX and free DOX in C6-ADR cells was compared. First, the internalization of iron by C6-ADR cells was characterized using the Ferrozine assay to ensure that DOX was delivered by cellular internalization of NP-DOX, rather than passive diffusion of released DOX from extracellular space. NP-DOX showed significant amounts of internalization (2.24±0.09 pg/cell) 4 hours after NP-DOX treatment (FIG. 5A). A decline in the intracellular iron concentration was observed at 24 hours after treatment (1.42±0.15 pg/cell), which could be attributed to the cell divisions. The iron content per cell is decreased as the number of cells is increased.

Figure 6A:
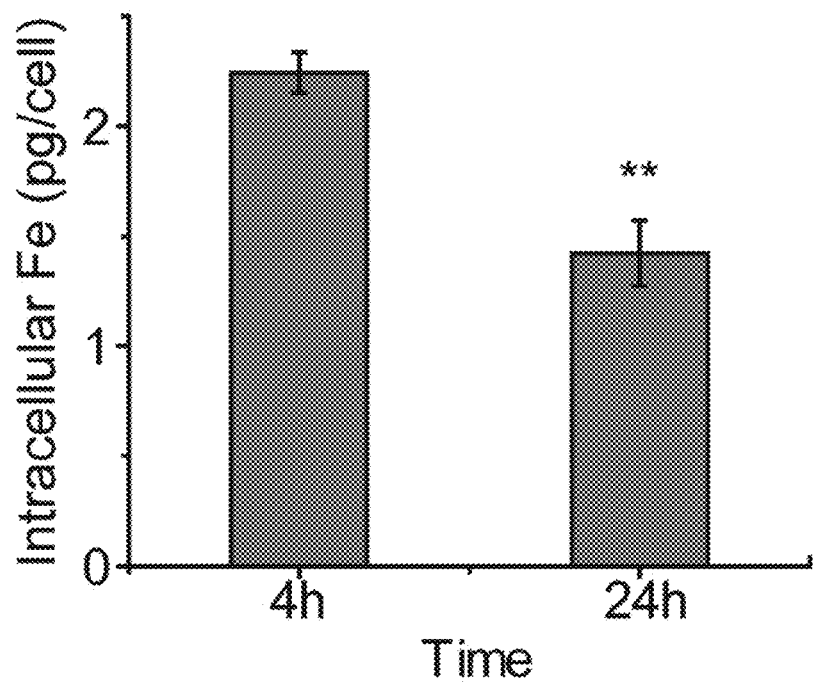
FIGS. 6A and 6B compare cellular internalization on free DOX and NP-DOX.
Figure 6B:
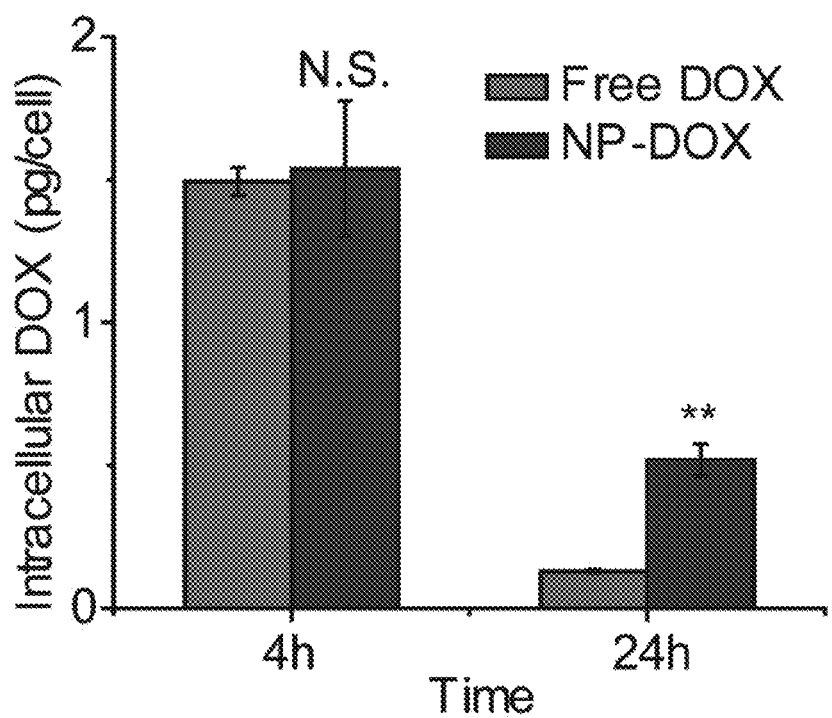

Concurrently, intracellular concentration of DOX was determined (FIG. 6B) by UV analysis. Four hours after treatment, the intracellular concentration of DOX was comparable between free DOX treated (1.49±0.05 pg/cell) and NP-DOX treated (1.54±0.24 pg/cell) C6-ADR cells. However, at 24 h after treatment, the intracellular concentration of DOX in cells treated with NP-DOX (0.52±0.06 pg/cell) was 4-fold higher than in cells treated with free DOX (0.13±0.01 pg/cell).

Figure 7:
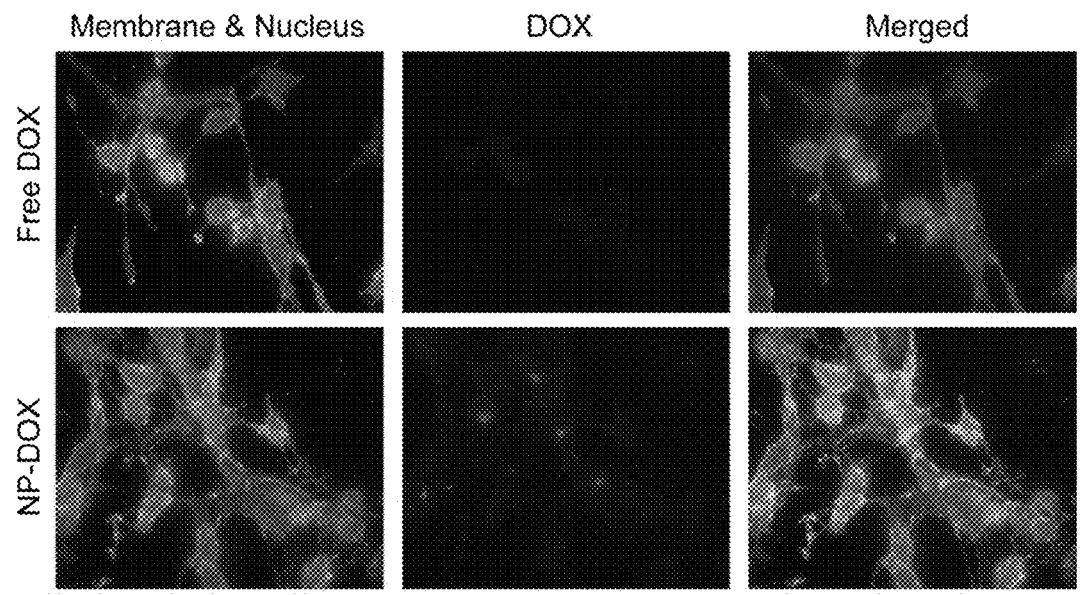
FIG. 7 compares fluorescence images of C6-ADR cells 24 h after the initial incubation with free DOX or NP-DOX, where cell nuclei were shown in blue, the DOX fluorescence in red, and cell membranes in green (WGA-AF488).
Figure 8:
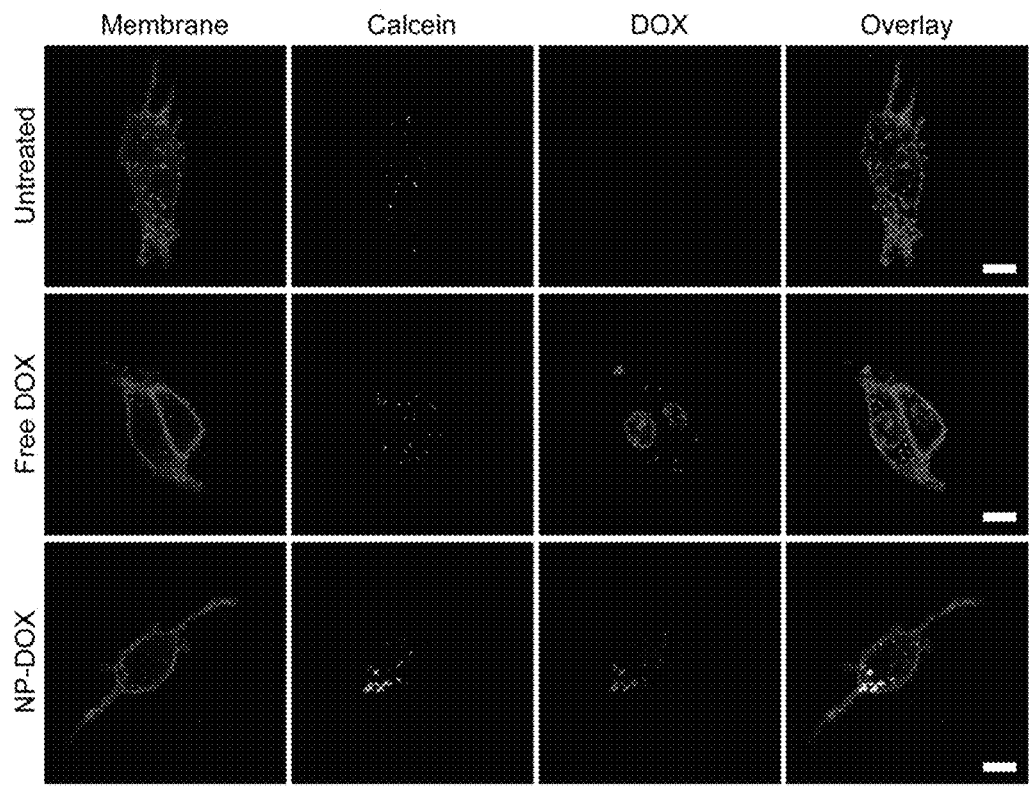
FIG. 8 compares confocal images of C6-ADR cells 4 h after incubation with either NP-DOX or free DOX. Endosomal compartments of cells were labeled with calcein (green, column 2), the DOX fluorescence was shown in red (column 3), and cell membranes in purple (WGA-AF647, column 1). The overlap of DOX and calcein signals, which yields yellow coloration (column 4), suggests that DOX resides in endosomal compartments. The scale bar corresponds to 10 μm.

The intracellular accumulation of free DOX and NP-DOX was further visualized by fluorescence microscopy (FIG. 7) after C6-ADR cells were treated with either DOX or NP-DOX for 4 h and fixed for another 20 h. Cells treated with free DOX had minimal fluorescence observed, while those treated with NP-DOX showed significant fluorescence signal in the perinuclear region of the cells. The internalization pathway of free DOX and NP-DOX were investigated by labeling endosomal compartments of cells with calcein after incubation with cells for 4 h. The colocalization of DOX and calcein signals was clearly observed for cells treated with NP-DOX (FIG. 8). For cells treated with free DOX, the DOX signal was partially colocalized with nucleus and partially localized in cytoplasma.

To reveal the mechanism for improved cell kill imparted by NP-DOX, the intracellular nanoparticle and DOX concentrations were monitored over time. Ferrozine assay results indicated that an initial uptake of free DOX by C6-ADR cells is similar to NP-DOX. However, the intracellular DOX concentration of cells treated with free DOX dropped precipitously (91% decrease) by 24 h after initial exposure, significantly lower than in cells treated with NP-DOX. The results suggest that ABC-transporters expressed in C6-ADR cells effectively reduced intracellular free DOX, while NP-DOX was able to maintain a substantial total DOX concentration (cleaved and conjugated DOX) after 24 h (about one third of the value of 4 h). Therefore, ABC transporter mediated MDR was mitigated by nanoparticle internalization and controlled release of drug. This prolonged release of drug likely accounts for the observed improvement in cell kill after 72 hrs. Visualization of C6-ADR cells by fluorescence microscopy further confirmed that NP-DOX aided in mitigating MDR in cancer cells. Because DOX is a small-molecule drug, free DOX can readily diffused into cells. Free DOX showed significant fluorescence at cell nuclei and near cell membrane right after treatment (FIG. 7), indicating rapid internalization of DOX and possible removal by ABC-mediated drug-efflux. Minimal fluorescence was observed 24 h after treatment (FIG. 7), indicating that free DOX was effectively removed by ABC-mediated drug-efflux. On the other hand, NP-DOX was much larger in size, and entered endosomes of cells by endocytosis, as shown in FIG. 8. Intracellular DOX signal was observed in the perinuclear region after 24 h (FIG. 7), suggesting a substantial amount of intracellular drug present. Sustained release of DOX from NP-DOX encapsulated by endosomes would result in higher cytotoxicity at 72 h.

In summary, in one aspect, the present invention provides a simple synthesis method to prepare theranostic nanoparticles for delivery of cancer chemotherapeutics and MR imaging. In certain embodiments, the nanoparticle includes a superparamagnetic iron oxide core that exhibits $T_2$ contrast enhancement with a hydrophilic and biodegradable PBAE polymer as coating. This nanoparticle system offers a platform based on a simple and highly controllable synthesis scheme that can be tailored to incorporate various therapeutic drugs, and adopt various drug release mechanisms such as reducing, enzymatic, or photolytic environments. The synthesis scheme is expected to dramatically improve the reproducibility of a nanoparticle formulation, and is easy and economical to scale up for mass production.

The following example is are provided for the purpose of illustrating, not limiting, the invention.

Example

Nanoparticle Preparation and Characterization

In this example, the preparation and characterization of a representative nanoparticle useful in the methods of the invention is described.

Materials

Doxorubicin.HCl (DOX), dopamine. HCl (DA), O,O'-bis (3-aminopropyl) diethylene glycol (BADG), di(ethylene glycol) diacrylate (DEGDA) and all general chemicals were purchased from Sigma-Aldrich (St. Louis, Mo.) unless otherwise specified. Methoxy-poly(ethylene glycol)-amine (mPEG-NH$_2$, MW 2,000) was purchased from Laysan Bio (Arab, Ala.). Dulbecco's modified Eagle media (DMEM), antibiotic-antimycotic (AA), WGA-AF488, Prolong Gold anti-fade reagent with DAPI and agarose gel were purchased from Invitrogen (Carlsbad, Calif.). Fetal bovine serum (FBS) was purchased from Atlanta Biologicals (Lawrenceville, Ga.).

Synthesis of PBAE Polymers

DOX-Loaded Polymer (PBAE-DOX).

Molar ratio of monomers was set at 50:19:19:12 (DEGDA:PEG:DA:DOX). To a 25 mL flask, 9 mg doxorubicin, 11.0 mg DEGDA, 32.8 mg mPEG-NH$_2$ and 7.8 mg DA were added. 5 µL Triethylamine dissolved in 1 mL DMSO were added to the flask, and the flask was sealed and purged with nitrogen. The reaction proceeded at 50° C. for 44 h. Excess amount (11 mg) of BADG was added to the flask to terminate the polymerization process. The reaction continued for 4 h and the product was precipitated by the organic solvent ether and dissolved in 2 mL of water. To remove any unreacted reactants, aqueous solution of PBAE-DOX was passed through a PD-10 column packed with Sephadex G-25 resin. The eluate was lyophilized to yield a final product as a dark red solid. Yield: 60.4%.

Control Polymer (without DOX).

To evaluate the intrinsic toxicity of nanoparticles without DOX, polymer with no DOX loading (PBAE-C) was prepared as described above for PBAE-DOX at a molar ratio of 50:25:25:0 (DEGDA:PEG:DA:DOX).

Synthesis of PBAE-DOX-Coated Iron Oxide Nanoparticles

Oleic acid capped iron oxide nanoparticles were synthesized as described in S. Sun, H. Zeng, D. B. Robinson, S. Raoux, P. M. Rice, S. X. Wang and G. Li, *J Am Chem Soc*, 2004, 126, 273-279.

The iron concentration of nanoparticles was determined by ICP-AES. The PBAE-DOX was coated to nanoparticle surface via ligand exchange reaction. 20 mg PBAE polymer was dissolved in 200 µL of DMSO and mixed with 1.8 mL of THF containing 2 mg nanoparticles. The mixture was placed in a flask, sealed and purged with nitrogen. The mixture was allowed to react for 24 h at 50° C. in dark. Nanoparticles were precipitated by ether and then redispersed in DMSO for long-term storage. Before experiments, nanoparticles were precipitated again by ether and then redispersed in D.I water. Centrifugal filters were used to remove any unbound polymer and residual organic solvents. The concentrated nanoparticles were diluted with D.I. water to 100 µg/mL equivalent concentration of drug.

Nanoparticle Characterization

The size and zeta potential of nanoparticles were measured by dynamic light scattering (DLS) using a DTS Zetasizer Nano (Malvern Instruments, Worcestershire, UK). Nanoparticles concentrations were 100 µg/mL for all measurements. Nanoparticle stability was determined in DMEM containing 10% FBS and 1% AA.

Drug loading was determined by measuring the absorbance of polymer or dissolved NPs solutions by a UV-vis spectrometer (Agilent Technologies, Santa Clara, Calif.). The wavelength of UV absorption for DOX was 494 nm. Fluorescence measurements were conducted with a SpectraMax M2 microplate reader (Molecular Devices, Union City, Calif.) using excitation and emission wavelengths of 485 nm and 590 nm, respectively, for DOX.

Samples for $^1$H-NMR analysis were prepared by dissolving 50 µg of nanoparticles in 50 µL of DCl and then diluted with 950 µL of D$_2$O, NMR spectra were acquired by a Avance 300 spectrometer (Bruker Corporation, Billerica, Mass.) operating at 300 MHz ($^1$H) and 298 K, with number of scans=128, acquisition time=1 s, relaxation delay (D1)=7 s.

For the measurement of the drug release profile, nanoparticle samples were loaded in dialysis devices (Slide-A-Lyzer MINI dialysis unit, 100 µL capacity, 2,000 MWCO, Pierce Biotechnology, Rockford, Ill.), and dialyzed against 10 mL PBS buffer at pH 7.4 or 4.5. Aliquots of samples were taken at 4 h, 24 h, 48 h, 60 h and 72 h. The fluorescence measurement was conducted using a microplate reader set to the same parameters described above.

Cell Culture

Rat glioma C6 cells were purchased from American Type Culture Collection (ATCC, Manassas, Va.) and maintained in DMEM containing 10% FBS and 1% antibiotic-antimycotic. DOX-resistant C6 cells (C6-ADR) were prepared from rat glioma C6 cells as described in F. M. Kievit, F. Y. Wang, C. Fang, H. Mok, K. Wang, J. R. Silber, R. G. Ellenbogen and M. Zhang, *J Control Release*, 2010. C6-ADR cells were then frozen and stored in liquid nitrogen. Fresh aliquots of C6-ADR were used for experiments to ensure that C6-ADR did not lose their drug resistance.

Dose-Response Experiments

C6-ADR cells were plated at 10,000 cells per well in 96-well plates the night before treatment. Cells were then treated with free DOX or NP-DOX at 0, 10, 50, 100, 1000, and 10000 ng/mL DOX in 150 µL fully supplemented DMEM for 4 hrs before washing three times with PBS and adding 150 µL fresh fully supplemented DMEM. Cell viability was determined at 24, 48, and 72 hrs post-treatment using the Alamar Blue viability assay following the manufacturer's protocol. IC50 values were calculated from dose-response curves generated with a polynomial dose-response approximation using the Origin software package (OriginLab Corporation, Northampton, Mass.).

Quantification of Cellular Internalization of Nanoparticles and DOX

Sensitive C6 and C6-ADR cells were plated at 100,000 cells per well in 24-well plates the night before treatment. Cells were then treated with 1000 ng/mL free DOX or equimolar concentration of DOX on NP-DOX in 1 mL fully supplemented DMEM for 4 hrs before cells were washed three times with PBS and 1 mL fresh fully supplemented media added. The cell number per well was assessed using the Alamar Blue and calculated based on a previously prepared standard curve. At 4 hr and 24 hr time points, cells were solubilized with 100 µL concentrated HCl and further diluted with 400 µL of D.I. water. The concentration of intracellular iron was determined by the colorimetric Ferrozine iron quantification assay with modifications. To 300 µL of cell lysate, 200 µL of 4M NaOH, 400 µL of D.I. water and 90 µL of Ferrozine solution were added. The solution was vortexed, transferred to 96-well plates, and the absorbance of 562 nm was recorded. The iron concentration per cell was calculated based on a standard curve of iron and cell number from Bradford protein assay. At the same time, the concentration of DOX was determined by fluorimetric measurement with a microplate reader, using excitation and emission wavelengths of 485 nm and 590 nm, respectively.

Fluorescence Imaging

C6-ADR cells were plated at 500,000 cells per well in 6-well plates containing 22×22 mm glass cover slips the night before treatment. Cells were treated with 1000 ng/mL free DOX or NP-DOX with equimolar concentration of DOX in 2 mL fully supplemented DMEM for 4 hrs before cells were washed three times with PBS and 2 mL fresh fully supplemented media added. After 24 hrs, cells were washed three times with PBS, and fixed in 4% formaldehyde (Polysciences Inc., Warrington, Pa.) for 30 min. Cell membranes were stained with wheat germ agglutinin, Alexa Fluor 488 conjugates (WGA-AF488, Invitrogen, Carlsbad, Calif.) following the manufacturer's protocol. The cover slips were then mounted on microscope slides using Prolong Gold anti-fade solution (Invitrogen, Carlsbad, Calif.) containing DAPI for cell nuclei staining. Images were acquired on an inverted fluorescent microscope (Nikon Instruments, Melville, N.Y.) with the appropriate filters using a Nikon Ri1 Color Cooled Camera System and 60× oil objective Lens. For internalization pathway experiment, cells were treated with DOX or NP-DOX in the presence of 0.25 mM calcein for 4 hrs. Cell membranes were stained with WGA-AF647 conjugate. DOX and calcein uptake were analyzed using confocal microscopy (Zeiss 510 Meta).

MR Imaging $T_2$ relaxation measurements were performed on a 4.7-T Bruker magnet equipped with Varian Inova spectrometer (Varian, Inc., Palo Alto, Calif.). Samples of NP-DOX were suspended in 1% agarose at concentrations of 0, 0.0625, 1.25, 2.5, and 5 µg Fe/ml. A 5 cm volume coil and a spin-echo imaging sequence were used to acquire $T_2$-weighted images. Images were acquired using a repetition time (TR) of 3000 ms and echo times (TE) of 13.6, 20.0, 40.0, 60.0, 80.0 and 120.0 ms. The spatial resolution parameters were: acquisition matrix of 256×128, field-of-view of 35×35 mm, section thickness of 1 mm and two averages. The $T_2$ maps were generated by NIH ImageJ (Bethesda, Md.) based on the equation, SI=A·exp($-TE/T_2$)+B, where SI is the signal intensity, TE is the echo time, A is the amplitude, and B is the offset. $R_2$ maps were generated by taking the reciprocal of $T_2$ maps.

Statistical Analysis

All experiments were run in triplicate and acquired data were expressed as mean±standard deviation. Statistical significance was determined using Student's t-test. Values of * P<0.05,  P<0.01, and * P<0.001 were considered significant.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nanoparticle, comprising:
   (a) a core having a surface and comprising a core material; and
   (b) a poly(beta-amino ester) directly coupled to the surface of the core, wherein the poly(beta-amino ester) comprises a poly(beta-amino ester) backbone having one or more therapeutic agents and one or more anchoring groups covalently coupled thereto, and wherein the poly(beta-amino ester) is not coupled to the surface of the core through an RNA.

2. The nanoparticle of claim 1, wherein the poly(beta-amino ester) has the formula:

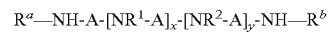

wherein

A has the formula —$CH_2CH_2C(=O)O$-L-$OC(=O)CH_2CH_2$—, wherein L is a group linking the ester moieties;

$R^1$ is a pendant group comprising a therapeutic agent;

$R^2$ is a pendant group comprising an anchoring group;

x is an integer from 1 to about 599;

y is an integer from 1 to about 599;

x+y is less than or equal to about 600; and $R^a$ and $R^b$ are independently selected from $R^1$ and $R^2$.

3. The nanoparticle of claim 2, wherein L is —$CH_2CH_2OCH_2CH_2$—.

4. The nanoparticle of claim 1 further comprising a polyalkylene oxide group pendant from the poly(beta-amino ester) backbone.

5. The nanoparticle of claim 4, wherein the poly(beta-amino ester) has the formula:

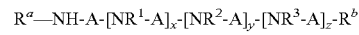

wherein

A has the formula —$CH_2CH_2C(=O)O$-L-$OC(=O)CH_2CH_2$—, wherein L is a group linking the ester moieties;

$R^1$ is a pendant group comprising a therapeutic agent;

$R^2$ is a pendant group comprising an anchoring group;

$R^3$ is a pendant group comprising a polyalkylene oxide group;

x is an integer from 1 to about 598;

y is an integer from 1 to about 598;

z is an integer from 1 to about 598;

x+y+z is less than or equal to about 600; and $R^a$ and $R^b$ are independently selected from R', $R^2$, and $R^3$.

6. The nanoparticle of claim 5, wherein L is —$CH_2CH_2OCH_2CH_2$—.

7. The nanoparticle of claim 4, wherein the polyalkylene oxide group is a polyethylene oxide group.

8. The nanoparticle of claim 1, wherein the therapeutic agent is selected from the group consisting of a small organic molecule, a peptide, an aptamer, a protein, and a nucleic acid.

9. The nanoparticle of claim 1, wherein the therapeutic agent is a chemotherapeutic agent.

10. The nanoparticle of claim 1, wherein the anchoring group is a carboxylic acid, a hydroxamic acid, a phosphonic acid, or a hydroxybenzene.

11. The nanoparticle of claim 1, wherein the anchoring group is a 1,2-dihydroxybenzene group.

12. The nanoparticle of claim 1, wherein the anchoring group is a 4-(2-aminoethyl)benzene-1,2-diol group.

13. The nanoparticle of claim 1, wherein the core material comprises a material having magnetic resonance imaging activity.

14. The nanoparticle of claim 1 further comprising a targeting agent.

15. The nanoparticle of claim 1 further comprising a fluorescent agent.

16. A composition, comprising a nanoparticle of claim 1 and a carrier suitable for administration to a warm-blooded subject.

17. A method for introducing a therapeutic agent into a cell comprising contacting a cell with a nanoparticle claim 1.

18. A method for detecting cells or tissues by magnetic resonance imaging, comprising:
   (a) contacting cells or tissues of interest with a nanoparticle of claim 1; and
   (b) measuring the level of binding of the nanoparticle, wherein an elevated level of binding, relative to normal cells or tissues, is indicative of binding to the cells or tissues of interest.

19. A method for treating a tissue with a therapeutic agent, comprising contacting a tissue of interest with a nanoparticle of claim 1.

20. A method for making a nanoparticle having a poly(beta-amino ester) coating, comprising:
   (a) reacting one or more amine compounds having the formula $NH_2$—$R^1$ and one or more amine compounds having formula $NH_2$—$R^2$ with a compound having the formula $CH_2$=CH—C(=O)O-L-OC(=O)—CH=$CH_2$ to provide a poly(beta-amino ester) having the formula $R^a$—NH-A-[$NR^1$-A]$_x$-[$NR^2$-A]$_y$-NH—$R^b$ wherein
   A has the formula —$CH_2CH_2$C(=O)O-L-OC(=O)$CH_2CH_2$—;
   L is a group linking the ester moieties;
   $R^1$ is a group comprising a therapeutic agent;
   $R^2$ is a group comprising an anchoring group;
   x is an integer from 1 to about 599;
   y is an integer from 1 to about 599;
   x+y is less than or equal to about 600; and
   $R^a$ and $R^b$ are independently selected from $R^1$ and $R^2$; and
   (b) directly coupling the poly(beta-amino ester) to the surface of a nanoparticle having a core and a surface to provide a nanoparticle coated with a poly(beta-amino ester),
   wherein the poly(beta-amino ester) is not coupled to the surface of the nanoparticle through an RNA.

* * * * *